United States Patent
Horesh et al.

(10) Patent No.: US 9,361,519 B2
(45) Date of Patent: Jun. 7, 2016

(54) COMPUTATIONAL ARRAY CAMERA WITH DYNAMIC ILLUMINATION FOR EYE TRACKING

(71) Applicant: Intel Corporation, Santa Clara, CA (US)

(72) Inventors: Nizan Horesh, Caesarea (IL); Amir Bousany, Kadima (IL)

(73) Assignee: Intel Corporation, Santa Clara, CA (US)

( * ) Notice: Subject to any disclaimer, the term of this patent is extended or adjusted under 35 U.S.C. 154(b) by 126 days.

(21) Appl. No.: 14/228,371

(22) Filed: Mar. 28, 2014

(65) Prior Publication Data

US 2015/0278576 A1     Oct. 1, 2015

(51) Int. Cl.
*G06K 9/00* (2006.01)
*G06K 9/46* (2006.01)
*G06K 9/52* (2006.01)

(52) U.S. Cl.
CPC ............... *G06K 9/0061* (2013.01); *G06K 9/46* (2013.01); *G06K 9/4661* (2013.01); *G06K 9/52* (2013.01); *G06K 2009/4666* (2013.01)

(58) Field of Classification Search
None
See application file for complete search history.

(56) References Cited

U.S. PATENT DOCUMENTS

| | | |
|---|---|---|
| 2004/0005083 A1 | 1/2004 | Fujimura et al. |
| 2005/0024586 A1 | 2/2005 | Teiwes et al. |
| 2011/0150334 A1 | 6/2011 | Du et al. |
| 2011/0170060 A1 | 7/2011 | Gordon |

FOREIGN PATENT DOCUMENTS

| | | |
|---|---|---|
| JP | 2002341239 A | 11/2002 |
| WO | WO-2015148198 A1 | 10/2015 |

*Primary Examiner* — Atiba O Fitzpatrick
(74) *Attorney, Agent, or Firm* — Schwegman Lundberg & Woessner, P.A.

(57) ABSTRACT

Methods and systems for eye tracking are disclosed. One such method obtains a plurality of images of the eye from an array camera and detects glint positions and a pupil edge of the eye in the plurality of images. A distance from the array camera to the pupil edge may be estimated based on the glint positions. A pupil image may be generated based on selected ones of the plurality of images, the glint positions, and the estimated distance to the pupil edge. A pupil center position may be determined based on the pupil image and the glint positions.

19 Claims, 8 Drawing Sheets

COMPUTATIONAL ARRAY CAMERA WITH DYNAMIC ILLUMINATION FOR EYE TRACKING

BACKGROUND

Eye tracking devices may be limited by their light gathering ability and thus use relatively large imaging sensors and lenses. This may limit their integration into mobile devices due to the resulting z-height (e.g., thickness).

Remote eye tracking may be based on detecting reflections of known light sources on the cornea and determining an edge of the pupil. There may be a trade-offs between these uses. For example, it may be easier and more robust to detect a pattern of multiple reflections but such a pattern may hide at least some of the edge of the pupil.

There are general needs for improved eye tracking.

DETAILED DESCRIPTION

Remote eye tracking systems may be based on infrared (IR) illumination of the human eye. An IR image sensor can capture the image of the eye, process the image, and determine the pupil contour (e.g., essentially circular edge) as well as the locations of the glints (e.g., IR light reflection points on cornea). The precision and robustness of the gaze point may be based on the ability to measure the location of the pupil and light point reflection as accurately as possible.

One problem with the current approach is that the (pixel) intensity contrast between a dark pupil and a dark iris may be relatively small and thus the determination of the pupil contour (e.g., edge) may become difficult and inaccurate. In remote gaze tracking, especially in a mobile device, it may be desirable to track a user's eyes with a wide range of motion. Thus, the camera may need to have a relatively large field of view. This may create constraints for the optical system and the illumination power used. Thus, relatively large image sensors and lenses with a large aperture may be used in order to gather as much light as possible. This may result in a relatively large z-thickness of the camera as compared to the camera with the smaller sensor. Using an array of lenses associated with an array camera will reduce this z-thickness.

Additionally, dynamic illumination control of the eye during the gaze vector tracking may provide improved pupil detection that may also increase the accuracy of the gaze vector tracking.

Figure 1:
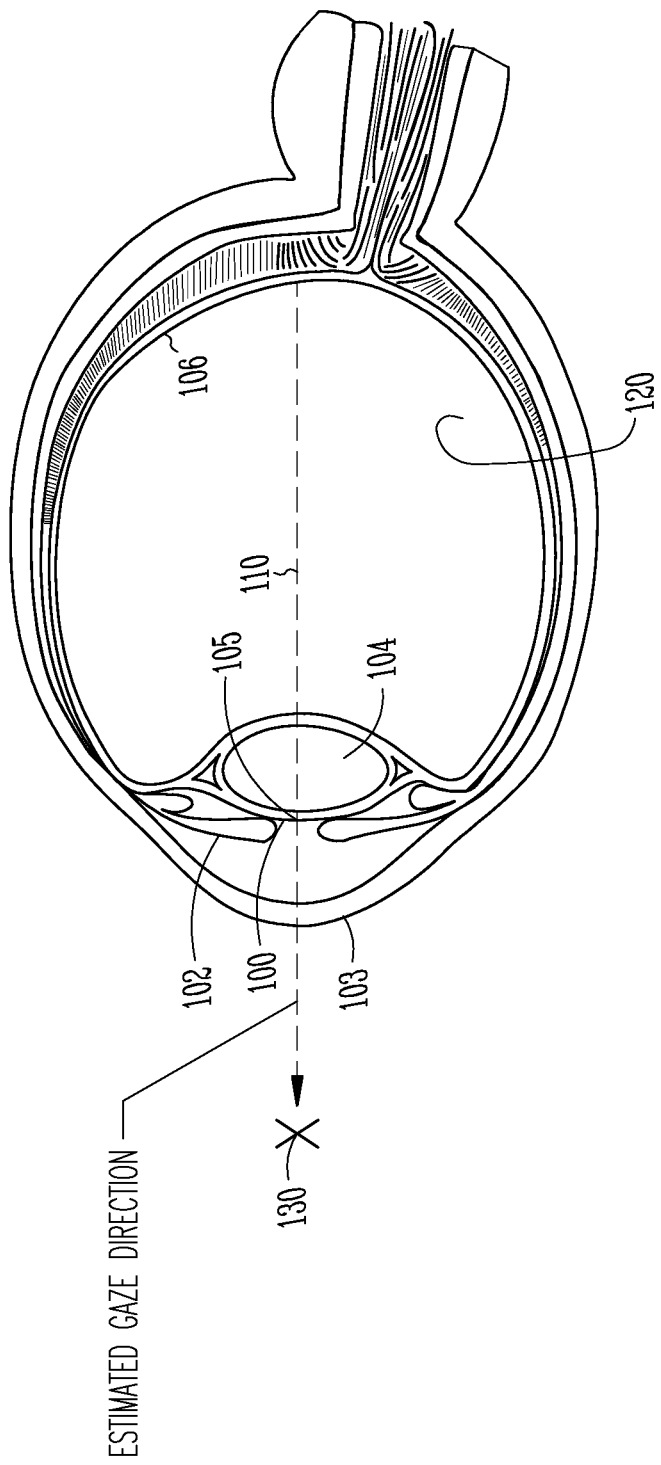
FIG. 1 shows a cross-sectional diagram of a portion of a human eye with a gaze vector.

FIG. 1 illustrates a cross-sectional view of a human eye. The pupil 100 is centrally located behind the cornea 103 and surrounded by the iris 102. A lens 104 separates the pupil 100 from the fluid-filled portion of the eye 120. The lens 104 focuses the light entering the eye onto the retina 106. The present embodiments may be based on finding the center 105 of the pupil 100 in order to estimate the gaze vector 110 and find the user's gaze point 130.

Figure 2:
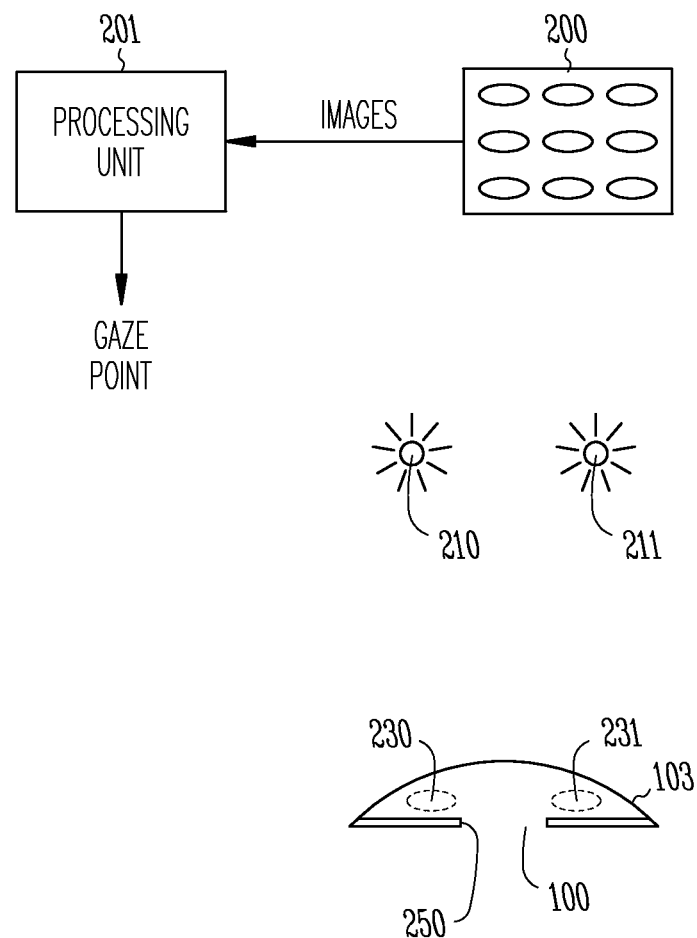
FIG. 2 shows a diagram of an embodiment of an eye tracking system.

FIG. 2 illustrates an embodiment of an eye tracking system. The system may include an array camera 200 coupled to a processing unit 201 (e.g., processor, computer). An embodiment of a processing unit 201 is discussed subsequently with reference to FIG. 7. The various modules of the processing unit 201 may be operated independently of any other module of the processing unit 201. Not all of the modules may be used.

A plurality of light sources 210, 211 (e.g., IR light sources) may generate a plurality of glints 230, 231 that are virtual images of the light sources. When the camera moves, the location of the glints 230, 231 will be changed as well. In an embodiment, two or more light sources 210, 211 may be used. Other embodiments may use a plurality of light sources that are dynamically controlled, as described subsequently with reference to FIGS. 4 and 5.

An array camera 200 includes an image sensor having a plurality of lenses (lens array), each lens formed over a particular area of the image sensor. The plurality of lens/sensor areas may capture a plurality of smaller images as compared to a single lens over the entire image sensor. Another embodiment of an array camera 200 may include a plurality of image sensors, each having a lens.

Figure 3:
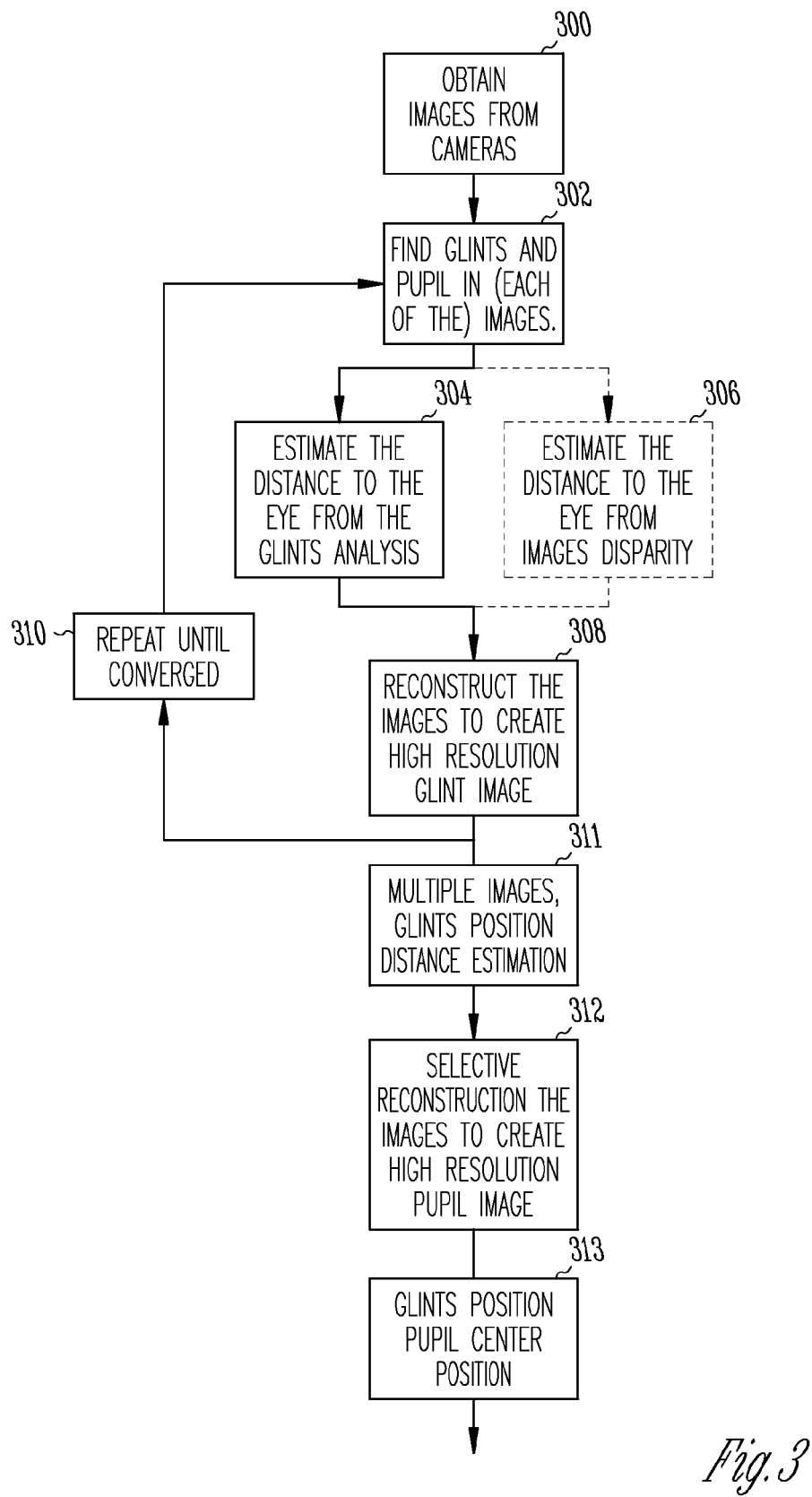
FIG. 3 shows a flowchart of an embodiment of a method for eye tracking in accordance with the system of FIG. 2.

The processing unit 201 may be configured to execute the method illustrated in the flowchart of FIG. 3. The method may determine an estimation of a pupil center of the user's eye and a corneal center of curvature (or some other location on the eye optical axis such as a nodal point of the lens) and, thus, determine a gaze vector and gaze point of a user.

Referring to FIG. 3, the multiple images may be obtained substantially simultaneously from the array camera (block 300). The glints 230, 231 and the pupil edge 250 (see FIG. 2) may be detected in each of the images (block 302). This may be accomplished using typical image processing techniques.

Using the determined positions of the glints 230, 231 in each image, the known location of the array camera 200 relative to the light sources 210, 211, the optical properties of the camera 200, the corneal curvature, the 3D position of the corneal center of curvature, and the 3D distance of the pupil edge to estimate a 3D distance (block 304) of the eye from the array camera 200. The 3D position of the eye, which is an absolute measure, may be the same for all the cameras. The corneal radius of curvature and the distance of the pupil edge from the corneal center of curvature may be estimated using known calibration methods.

The 3D position of the pupil may be determined from the 3D position of the corneal center of curvature by first assuming a standard known (or calibrated) distance from the pupil plane to the corneal center of curvature (CCC). The corneal radius of curvature and the cornea refractive index are also known. By back-projecting the pupil edge from the camera to the 3D world, the actual pupil will be at an intersection of the back-projected rays and the pupil plane. Using an optimization method, the pupil edge (at know distance from the CCC) can be found that will create a consistent image of the pupil. Some embodiments may estimate the distance to the pupil edge by adding the distance from the pupil plane to the computed CCC, assuming that the optical axis is known with some accuracy. Considering that the distance from the pupil plane to the CCC is approximately 4 mm, the error of this estimation may be approximately 4 mm*Sin(θ) where θ is the uncertainty in the optical axis orientation (e.g., for θ=10°, the error may be approximately 0.7 mm).

In another embodiment, the distance to the eye may be estimated by disparity analysis, as a result of parallax error, of the multiple images (block 306). The parallax error is the difference in pupil edge location as seen by each of the individual cameras of the array that results from the cameras' translational separation. The relative position of each of the cameras is known by pre-calibration. The disparity between the pupil edge can be used to determine a 3D position of the pupil edge. For example, one such method for calculating the 3D position of the pupil edge from a pair of images may be referred to in the art as triangulation. Some embodiments can take into consideration the refractive properties of the cornea that affect the optical path to the glints. The 3D estimation of the location of the eye from steps 304 or 306 may be combined into a more accurate estimation.

Given the 3D position of the pupil, the distance of the pupil from the cameras, and the known camera geometry, the multiple images may be combined to synthesize a high resolution, intermediate image of the eye region (block 308). This process may be referred to in the art as super-resolution that generates an image having a higher resolution than any of the originally obtained images. The glints are virtual images of the light source. Considering this, their disparity may be modeled separately, as reflections of light from a known spherical surface.

The synthesized high resolution image, with the estimated distance of the pupil from the camera, may be fed back to the initial step 302 of finding the glints and pupil in each image. The method repeats until the process has converged (block 310) (e.g., the changes in the estimated distance of the pupil edge are below some predetermined threshold of changes).

The glints in the images may occasionally cross the pupil edge and, thus, obscure it in the image. This may increase the noise in the pupil center estimation. In order to reduce this noise, the originally obtained images (block 300) and the 3D information obtained previously (e.g., glint position, pupil plane distance estimation) may be provided (block 311) for selective reconstruction of the pupil image to create a relatively high resolution pupil image (block 312). The selective reconstruction may include dividing the eye image into sub-region (e.g. pixels). For each sub-region a subset of the multiple images will be selected by rejecting the images with a glint in the sub-region (e.g., the glint obscures the pupil edge). For each sub-region, the selected subset will be used to reconstruct the high resolution image, with a selected point of view (typically, the center of the camera array). The result is a relatively high resolution image of the pupil, with minimal interference from the glints. This image may be further analyzed to find the pupil center accurately (block 313). The position of the cornea center of curvature may not be estimated directly from this image (the information from the glints is minimal here), but taken from the previous steps.

Any of a plurality of methods may be used to determine the gaze vector from the determined glint positions and pupil center position. For example, an eyeball model using Purkinje images, a global head model, or an active appearance model may be used. The present embodiments are not limited to any one model.

Figure 4:
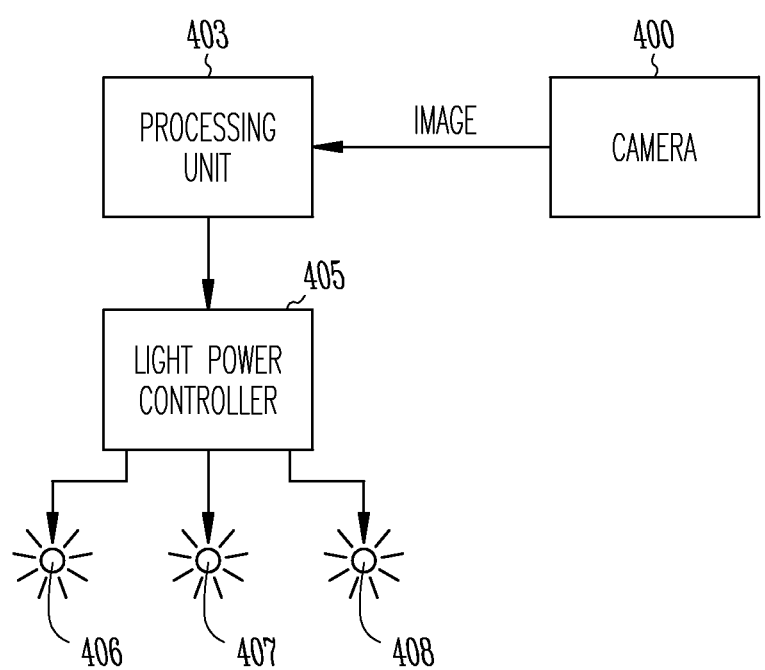
FIG. 4 shows a diagram of an embodiment of an eye tracking system having dynamic illumination activation.

FIG. 4 illustrates a diagram of an embodiment of an eye tracking system having dynamic illumination activation. The system includes a camera 400 for capturing at least one image. In an embodiment, the camera 400 may be an array camera, as discussed previously. The array camera may include multiple lenses over an image sensor or multiple image sensors each having a separate lens. If IR illumination is used, the image sensor(s) would be IR sensitive sensors.

The camera is coupled to a processing unit 403 (e.g., processor, computer) that may access the images from the camera 400. An embodiment of a processing unit 403 is discussed subsequently with reference to FIG. 7.

A light power controller 405 is coupled to the processing unit 403 and may be responsible for dynamic control of power to the coupled light sources 406-408 (e.g., IR light sources). Based on the method of FIG. 6, the light power controller 405 may dynamically activate/deactivate the light sources 406-408 individually. In an embodiment, the light power controller 405 may be part of the processing unit 403. Another embodiment may implement the light power controller 405 as a separate module.

The light sources 406-408 may be IR light emitting diodes (LEDs). Other embodiments may use other parts of the electromagnetic spectrum. In an embodiment, two or more light sources may be used to provide an adequate light pattern for tracking the pupil of a user's eye.

The system of FIG. 4 may have two modes: an eye detection mode and an eye tracking mode. In the eye detection mode, the system may search for the user's eyes by attempting to find the glint pattern on the eye that is generated by the known pattern of light sources 406-408. Since the location of the user's eyes is initially unknown, the system may search a relatively large field-of-view (FOV). Assuming a given glint pattern, the probability of finding a false glint may be referred to as $\rho$. The probability of finding a second glint in a position that matches the illumination pattern may be $\rho^2$ times the possible alignments of two light sources. Since $\rho$ may be relatively small and the number of possible alignments may be of an order of 1, it may be seen that having more active light sources may improve the detection robustness of the system.

The eye tracking mode assumes a successful completion of the eye detection mode. During the eye tracking mode, the light sources may be dynamically switched on or off, as discussed subsequently with reference to the method of FIG. 6, in order to reduce the interference of the glints with the pupil edge.

Figure 5:
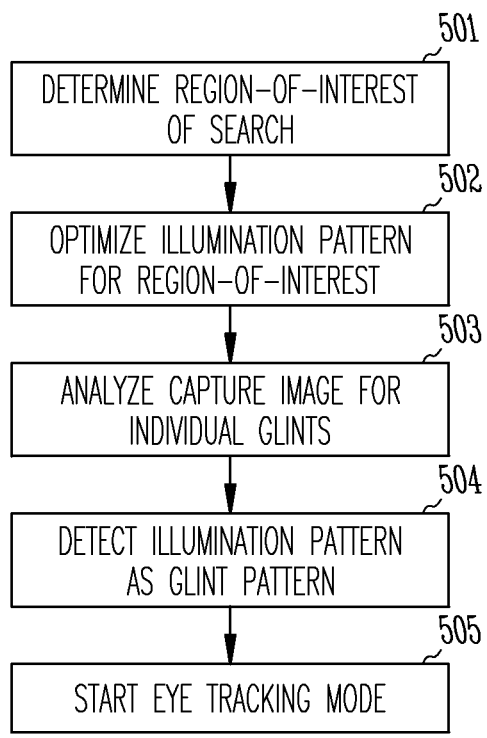
FIG. 5 shows a flowchart of an embodiment of a method for eye detection in accordance with the system of FIG. 4.

FIG. 5 illustrates a flowchart of an embodiment of a method for eye detection. A region-of-interest (ROI) for the search may be initially determined 501. The ROI may be the entire FOV of the camera(s) or a sub-region based on information from a head or face tracking mechanism. The sub-region may also be based on eye tracking information from results of a previous eye tracking operation.

The illumination pattern may be optimized for the ROI 502. The location and optical characteristics of the light sources may be known in advance. Since some of the light sources may not illuminate the entire FOV, only those light sources that may illuminate the ROI may be selected to be activated.

Once the selected light sources are activated, the resulting image capture from the search may be analyzed 503. The image may first be searched for individual glints by detection of small regions of high intensity light relative to the background. This process may use only a small amount of computations but may generate a relatively large number of false glints.

Since the generated illumination pattern is known, the set of detected glints may now be searched for the corresponding reflected illumination pattern 504 (e.g., glint pattern that matches the illumination pattern). This type of matching may be referred to in the art as point pattern matching and may be performed in multiple ways.

Once an eye (or pair of eyes) has been detected with relatively high confidence, the eye tracking mode can be implemented 505. The eye tracking mode may be part of the dynamic illumination activation method illustrated in FIG. 6.

Figure 6:
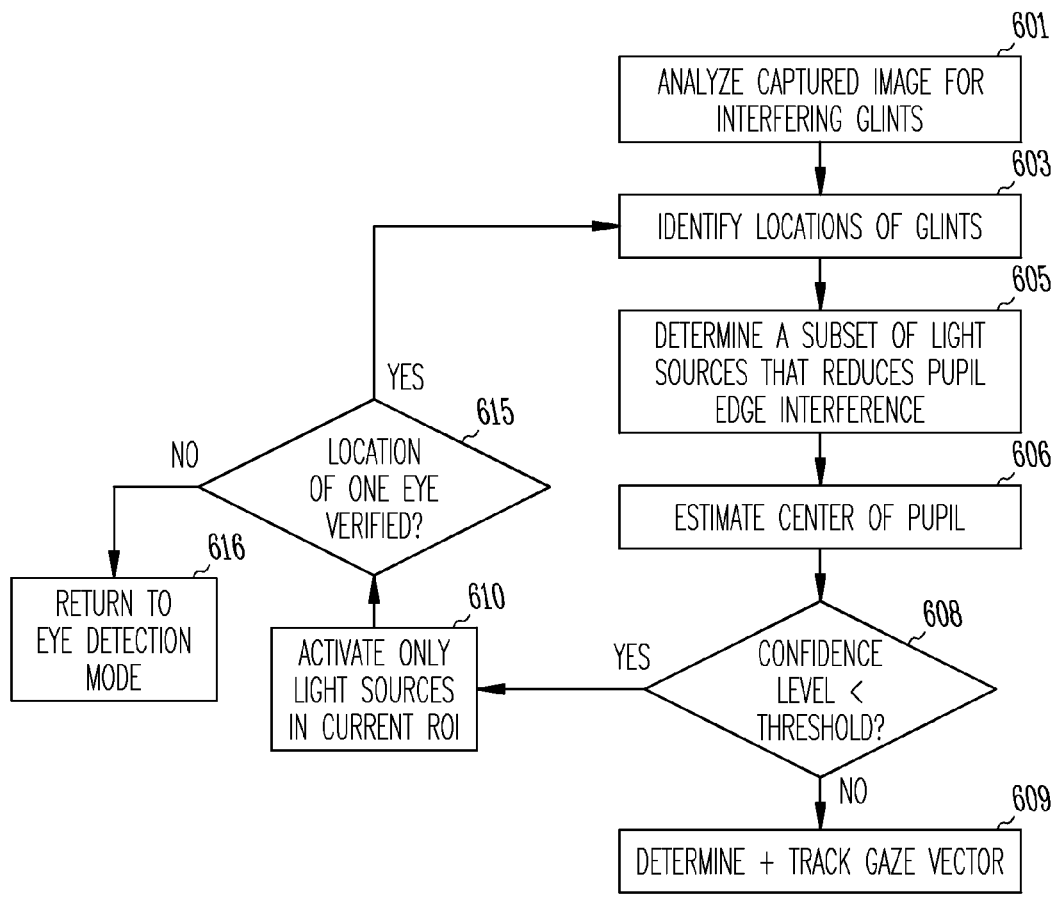
FIG. 6 shows a flowchart of an embodiment of a method for dynamic illumination activation in accordance with the system of FIG. 4.

FIG. 6 illustrates a flowchart of an embodiment of a method for dynamic illumination activation in accordance with the system of FIG. 4 and the eye detection method of FIG. 5. During the eye tracking, the method for dynamic illumination activation may be used to deactivate selected light sources in order to reduce interference of glints with the pupil's edge.

The eye image(s), from the eye detection method of FIG. 5 using a detection module 762 (see FIG. 7), may be analyzed and the glints that interfere with the pupil edge may be identified 601. An analysis module 761 (see FIG. 7) may be used for this function. Based on the location of the eye, as computed from the images of the glint pattern, the location of the glints from all of the light sources, active or not, can be identified 603.

A subset of the light sources that may reduce interference with the pupil's edge may be determined 605. This may be accomplished in a mathematical way by minimizing the variance of the pupil center estimation 606. This variance can be estimated by the inverse of the Fisher information matrix of the ellipse parameters. The variance of the estimated ellipse center may be minimized by selecting the subset of light sources such that 1) there are at least two glints; and 2) the variance of the pupil center, as calculated from the Fisher information matrix, may be minimized as in the following:

$$\mathrm{ArgMin}_{Light\ Source\ Activation\atop s.t.\#of\ glints \geq 2} (\mathrm{Var}[X_{pupil}] + \mathrm{Var}[Y_{pupil}])$$

Once the center of the pupil has been identified, the gaze vector may be determined and tracked 609 by methods identified previously. A tracking module 763 (see FIG. 7) may be used to perform this function.

If, during the tracking mode, the confidence level of the tracking drops below a predetermined confidence threshold 608. The confidence level may be defined as one over the variance of the pupil center. The dynamic illumination activation may activate only those light sources corresponding to the current image ROI 610. The confidence level may be estimated by analyzing the variance of the gaze vector, which is a function of the center of pupil variance and the cornea center of curvature variance. Another embodiment of a method to estimate the confidence level may analyze the temporal noise of the gaze point. This may be used to verify the location of the eyes and, thus, reject false detection and increase the confidence level of the tracking mode. If the dynamic activation of the light sources verifies at least one eye 615, the method may then repeat from identifying the locations of the glints 603.

If the dynamic activation of the light sources does not verify the location of at least one eye 615, the method may return to the eye detection mode 616. The method may then repeat the execution of the embodiment of FIG. 5.

Figure 7:
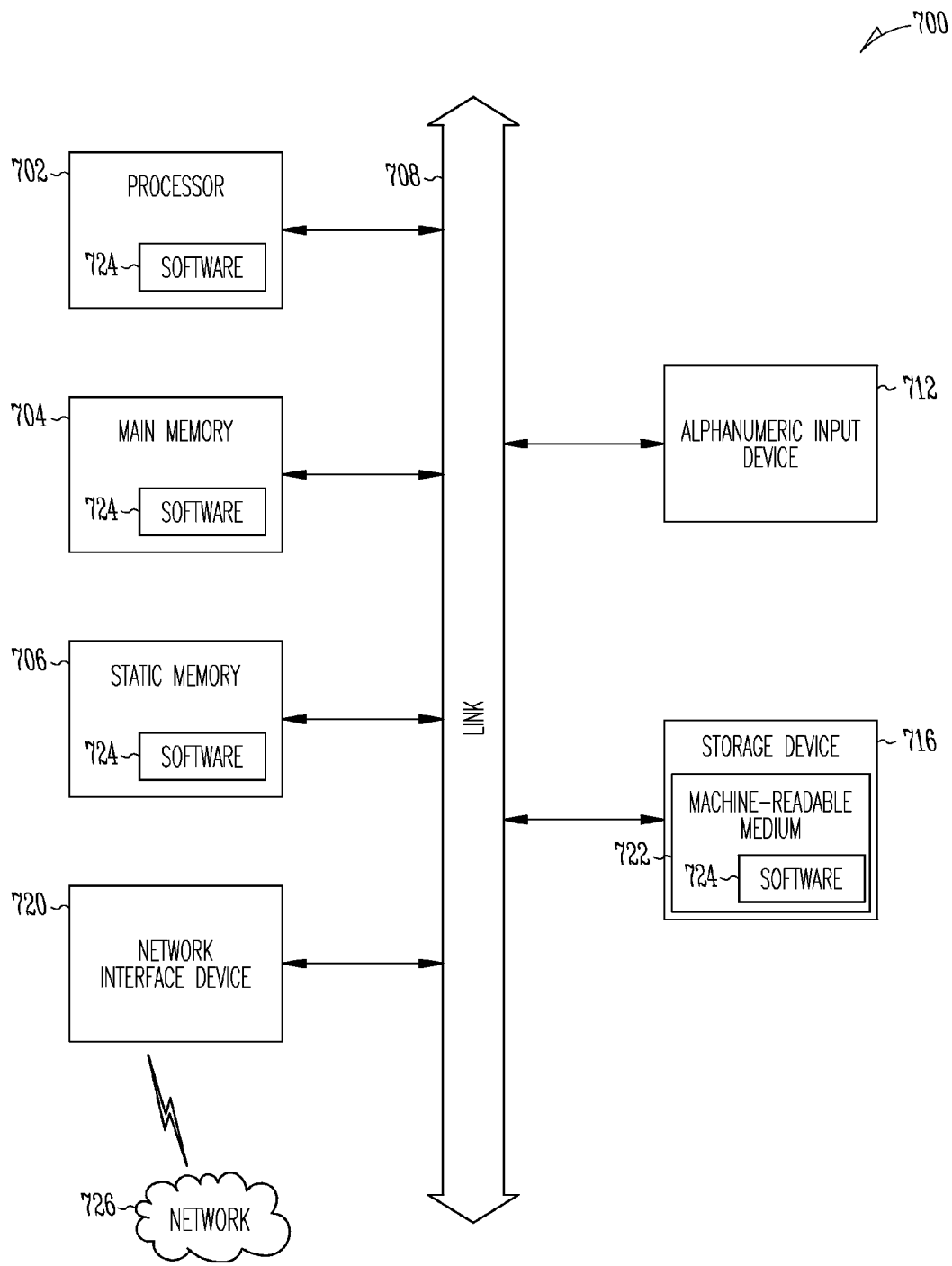
FIG. 7 shows a block diagram of an embodiment of a processing unit in accordance with the systems of FIGS. 2 and 4.

FIG. 7 is a block diagram illustrating a machine in the example form of a processing unit 700, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a wearable electronic device, an onboard vehicle system, personal computer (PC), a tablet PC, a hybrid tablet, a personal digital assistant (PDA), a mobile telephone, or any machine capable of executing instructions (sequential or otherwise) that specify actions to be taken by that machine. Further, while only a single machine is illustrated, the term "machine" shall also be taken to include any collection of machines or modules that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

As used herein, the term "module" can refer to software/firmware, hardware, or a combination of software/firmware and hardware. Each module can include its own controller circuit for executing any software/firmware resident in the module. The modules may be part of the processing unit 700 or operated separate from the processing unit 700. The modules may be operated serially, in parallel, or in a distributed fashion.

An example processing unit 700 includes at least one processor 702 (e.g., a central processing unit (CPU), a graphics processing unit (GPU) or both, processor cores, compute nodes, etc.), a main memory 704 and a static memory 706, which communicate with each other via a link 708 (e.g., bus). The processing unit 700 may further include an alphanumeric input device 712 (e.g., a keyboard). The processing unit 700 may additionally include a storage device 716 (e.g., a drive unit), a signal generation device 718 (e.g., a speaker), a network interface device 720, and one or more sensors (not shown).

The storage device 716 includes a machine-readable medium 722 on which is stored one or more sets of data structures and instructions 724 (e.g., software) embodying or utilized by any one or more of the methodologies or functions described herein. The instructions 724 may also reside, completely or at least partially, within the main memory 704, static memory 706, and/or within the processor 702 during execution thereof by the processing unit 700, with the main memory 704, static memory 706, and the processor 702 also constituting machine-readable media.

While the machine-readable medium 722 is illustrated in an example embodiment to be a single medium, the term "machine-readable medium" may include a single medium or multiple media (e.g., a centralized or distributed database, and/or associated caches and servers) that store the one or more instructions 724. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., WI-FI™, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Figure 8:
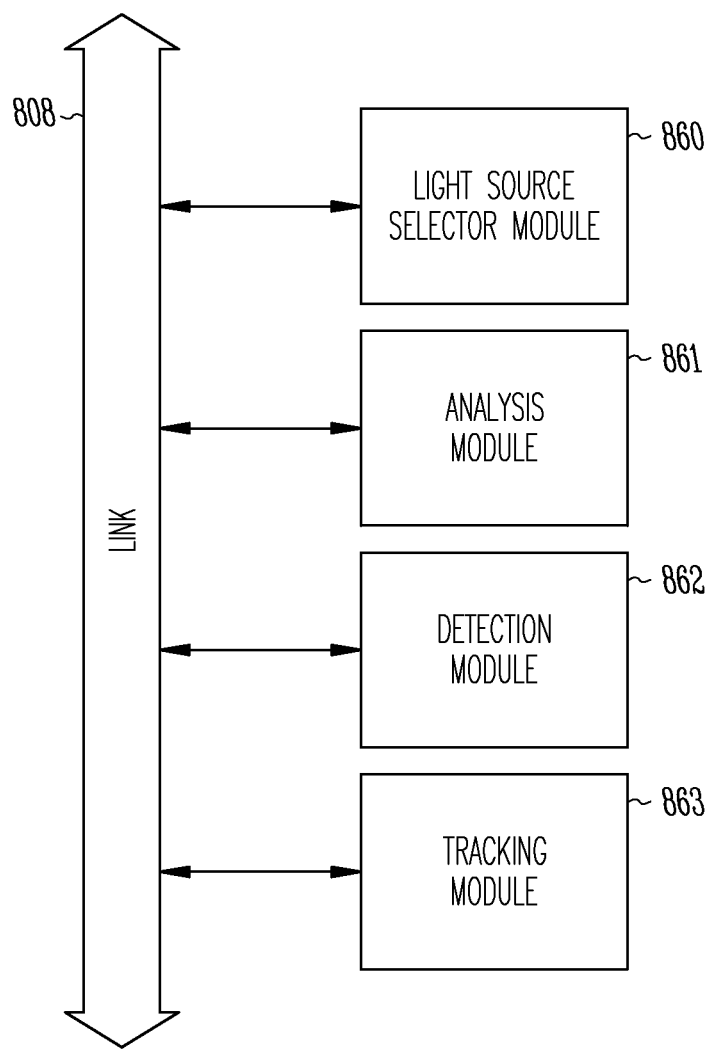
FIG. 8 shows a block diagram of another embodiment of a processing unit in accordance with the systems of FIGS. 2 and 4.

FIG. 8 illustrates another embodiment of a processing unit in accordance with the systems of FIGS. 2 and 4. A light source selector module 860 may provide selection of the light sources as described previously. An analysis module 861 may provide analysis of received glint data as described previously such as estimate a distance from the array camera, that generated the plurality of images, to the pupil edge based on a three-dimensional position of a corneal center of curvature of the eye. A detection module 862 may provide detection of glints based on data from the array camera as previously described. A tracking module 863 may provide analysis of glint position data for interfering glints and glint location as well as determining which light sources to select to remove the interfering glints.

EXAMPLES

Examples may include subject matter such as a method, means for performing acts of the method, at least one machine-readable medium including instructions that, when performed by a machine cause the machine to performs acts of the method, or of an apparatus or system for a computation array camera with dynamic illumination for eye tracking according to embodiments and examples described herein.

Example 1 is a method for eye tracking. The method comprises obtaining a plurality of images of the eye from an array camera; detecting glint positions and a pupil edge of the eye in the plurality of the images; estimating a three-dimensional distance from the array camera to the pupil edge based on the glint positions; generating a pupil image based on selected ones of the plurality of images, the glint positions, and an estimated distance to the eye based on the estimated distance from the array camera to the pupil edge; and determining a pupil center position based on the pupil image and the glint positions.

In Example 2, the subject matter of Example 1 can optionally include wherein obtaining the plurality of images of the eye comprises obtaining an image from each camera of the array camera.

In Example 3, the subject matter of Examples 1-2 can optionally include generating an intermediate image from the plurality of images, the intermediate image having a higher resolution than a single image of the plurality of images; and repeating detecting the glint positions and the pupil edge, estimating the distance to the pupil, and generating the intermediate image until a number of changes in the estimated distance to the pupil edge over a number of samples are less than a predetermined threshold of changes.

In Example 4, the subject matter of Examples 1-3 can optionally include wherein the pupil image has a higher resolution than any one of the plurality of images.

In Example 5, the subject matter of Examples 1-4 can optionally include wherein generating the pupil image comprises selecting one of the plurality of images in which the pupil edge is not obscured by a glint.

In Example 6, the subject matter of Examples 1-5 can optionally include wherein generating the pupil image comprises: dividing each of the plurality of images into sub-regions; and selecting a subset of the multiple images by rejecting the images with a glint in the sub-region.

In Example 7, the subject matter of Examples 1-6 can optionally include generating the glints from a plurality of light sources having an illumination pattern; deactivating selected light sources of the plurality of light sources based on interference with the pupil edge in the pupil image.

In Example 8, the subject matter of Examples 1-7 can optionally include wherein estimating the distance from the array camera to the eye based on the glint positions comprises determining a disparity in pupil edge location between the plurality of images.

In Example 9, the subject matter of Examples 1-8 can optionally include wherein detecting the pupil edge comprises detecting a three-dimensional position of the pupil edge based on the disparity in the pupil edge location between at least a pair of images from the plurality of images.

In Example 10, the subject matter of Examples 1-9 can optionally include determining a gaze vector based on the pupil center position, the glint positions, and one of an eyeball model using Purkinje images, a global head model, or an active appearance model.

Example 11 is a method for eye tracking comprising: obtaining a plurality of images comprising glints as generated by an illumination pattern; detecting a pupil edge in the plurality of images; determining a subset of light sources that reduces interference of the glints with the pupil edge while keeping a plurality of glints; estimating a center of the pupil; and tracking a gaze vector based on the estimate of the center of the pupil.

In Example 12, the subject matter of Example 11 can optionally include detecting the eye by: determining a region-of-interest, including the eye, for searching; adjusting the illumination pattern based on the region-of-interest; detecting the illumination pattern in the plurality of images as represented by a glint pattern; and tracking the eye based on the glint pattern.

In Example 13, the subject matter of Examples 11-12 can optionally include wherein adjusting the illumination pattern comprises activating and/or deactivating particular light sources such that only light sources producing glints in the region of interest are activated.

In Example 14, the subject matter of Examples 11-13 can optionally include wherein determining the subset of light sources that reduces interference of the glints with the pupil edge comprises deactivating particular light sources that interfere with the pupil edge.

In Example 15, the subject matter of Examples 11-14 can optionally include wherein determining the subset of light sources that reduces interference of the glints with the pupil edge comprises estimating a variance of the estimate of the center of the pupil by an inverse of a Fisher information matrix of ellipse parameters.

In Example 16, the subject matter of Examples 11-15 can optionally include wherein, when a confidence level of eye tracking becomes less than a predetermined confidence threshold, activating only those light sources corresponding to a current image region-of-interest.

In Example 17, the subject matter of Examples 11-16 can optionally include estimating a distance from an array camera to the eye based on the glints and triangulation.

Example 18 is a machine-readable medium comprising instructions for eye tracking, which when executed by a machine, cause the machine to: obtain a plurality of images of the eye from an array camera; detect glint positions and a pupil edge of the eye in the plurality of the images; estimate a distance from the array camera to the pupil edge based on the glint positions; generate a pupil image based on selected ones of the plurality of images, the glint positions, and an estimated distance to the eye based on the estimated distance from the array camera to the pupil edge; and determine a pupil center position based on the pupil image and the glint positions.

In Example 19, the subject matter of Example 18 can optionally include wherein the machine is further caused to estimate the distance of the pupil edge from the array camera based on the detected glint positions in each image, a location of the array camera relative to light sources, corneal curvature of the eye, and a three-dimensional position of a corneal center of curvature.

Example 20 is an eye tracking system comprising: an array camera to generate a plurality of images of the eye; a plurality of light sources to generate an illumination pattern represented by a glint pattern on the eye; and a processing unit, coupled to the array camera and the plurality of light sources, to obtain the plurality of images, detect a glint pattern representative of an illumination pattern generated by the plurality of light sources and a pupil edge of the eye in the plurality of images, estimate a distance from the array camera to the pupil edge based on a three-dimensional position of a corneal center of curvature of the eye, generate a pupil image based on selected ones of the plurality of images, the glint pattern, and an estimated distance to the eye, and determine a gaze vector based on the pupil image and the glint pattern.

In Example 21, the subject matter of Example 20 can optionally include wherein the processing unit is further to control deactivation of each of the plurality of light sources in response to a glint of the glint pattern interfering with the pupil edge in at least one of the plurality of images.

In Example 22, the subject matter of Examples 20-21 can optionally include wherein the processing unit is further to determine a region-of-interest within a field of view of the array camera and adjust the illumination pattern by activating or deactivating particular ones of the plurality of light sources to keep the illumination pattern within the region of interest.

In Example 23, the subject matter of Examples 20-22 can optionally include wherein the processing unit is further to generate the pupil image from the plurality of images such that the pupil image has a higher resolution than any one of the plurality of images.

In Example 24, the subject matter of Examples 20-23 can optionally include wherein the processing unit is further to generate the pupil image from the selected ones of the plurality of images such that only those images not having a glint interfering with the pupil edge are used in the pupil image.

In Example 25, the subject matter of Examples 20-24 can optionally include wherein the processing unit is further to generate a three-dimensional position of the pupil edge based triangulation from parallax error of the pupil edge in at least a pair of images of the plurality of images.

Example 26 is an eye tracking system comprising: a detection module configured to detect a glint pattern, representative of an illumination pattern generated by a plurality of light sources, and a pupil edge of an eye in a plurality of images; an analysis module coupled to the detection module and configured to estimate a distance from an array camera, that generated the plurality of images, to the pupil edge based on a three-dimensional position of a corneal center of curvature of the eye; and a processing module coupled to the analysis module and the detection module and configured to generate a pupil image based on selected ones of the plurality of images, the glint pattern, and an estimated distance to the eye, and determine a gaze vector based on the pupil image and the glint pattern.

In Example 29, the subject matter of Example 28 can optionally include comprising a light source selector module, coupled to the processing module, configured to activate and/or deactivate one or more of the plurality of light sources in response to a glint of the glint pattern interfering with the pupil edge in at least one of the plurality of images.

In Example 30, the subject matter of Examples 28-29 can optionally include comprising a tracking module coupled to the processing module and configured to track the gate vector.

In Example 31, the subject matter of Examples 28-30 can optionally include wherein the analysis module is further configured to determine a region-of-interest within a field of view of an array camera and adjust the illumination pattern by activating or deactivating particular ones of the plurality of light sources to keep the illumination pattern within the region of interest.

In Example 32, the subject matter of Examples 28-31 can optionally include wherein the processing unit is further to generate the pupil image from the plurality of images such that the pupil image has a higher resolution than any one of the plurality of images.

In Example 33, the subject matter of Examples 28-32 can optionally include wherein the processing unit is further to generate the pupil image from the selected ones of the plurality of images such that only those images not having a glint interfering with the pupil edge are used in the pupil image.

In Example 34, the subject matter of Examples 28-33 can optionally include wherein the processing unit is further to generate a three-dimensional position of the pupil edge based on triangulation from parallax error of the pupil edge in at least a pair of images of the plurality of images.

Example 35 is a system for eye detection comprising: a light source selector module configured to activate or deactivate one or more of a plurality of light sources in response to a glint of a glint pattern, generated by the plurality of light sources, interfering with a pupil edge of the eye in at least one of a plurality of images; a detection module, coupled to the light source selector module, configured to determine a region of interest in the plurality of images and detect an illumination pattern in one or more of the plurality of images and detect the eye based on the pupil edge of the eye; and an analysis module, coupled to the detection module and the light source selector module, configured to analyze the plurality of images for the glint pattern.

In Example 36, the subject matter of Example 35 can optionally include a tracking module, coupled to the light source selector module, the detection module, and the analysis module, configured to track the eye.

Example 37 is a method for eye tracking comprising: means for obtaining a plurality of images of the eye from an array camera; means for detecting glint positions and a pupil edge of the eye in the plurality of the images; means for estimating a three-dimensional distance from the array camera to the pupil edge based on the glint positions; means for generating a pupil image based on selected ones of the plurality of images, the glint positions, and an estimated distance to the eye based on the estimated distance from the array camera to the pupil edge; and means for determining a pupil center position based on the pupil image and the glint positions.

In Example 38, the subject matter of Example 37 can optionally include means for generating an intermediate image from the plurality of images, the intermediate image having a higher resolution than a single image of the plurality of images The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A method for eye tracking comprising:
    obtaining a plurality of images of the eye from an array camera;
    detecting glint positions and a pupil edge of the eye in the plurality of the images;
    estimating a three-dimensional distance from the array camera to the pupil edge based on the glint positions;
    generating a pupil image based on selected ones of the plurality of images, the glint positions, and an estimated distance to the eye based on the estimated distance from the array camera to the pupil edge; and
    determining a pupil center position based on the pupil image and the glint positions.

2. The method of claim 1, further comprising:
    generating an intermediate image from the plurality of images, the intermediate image having a higher resolution than a single image of the plurality of images; and
    repeating detecting the glint positions and the pupil edge, estimating the distance to the pupil, and generating the intermediate image until a number of changes in the estimated distance to the pupil edge over a number of samples are less than a predetermined threshold of changes.

3. The method of claim 1, wherein the pupil image has a higher resolution than any one of the plurality of images.

4. The method of claim 1, wherein generating the pupil image comprises:
    dividing each of the plurality of images into sub-regions; and
    selecting a subset of the multiple images by rejecting the images with a glint in the sub-region.

5. The method of claim 1, further comprising:
    generating the glints from a plurality of light sources having an illumination pattern; and
    deactivating selected light sources of the plurality of light sources based on interference with the pupil edge in the pupil image.

6. The method of claim 1, wherein estimating the distance from the array camera to the eye based on the glint positions comprises determining a disparity in pupil edge location between the plurality of images.

7. The method of claim 1, wherein detecting the pupil edge comprises detecting a three-dimensional position of the pupil edge based on the disparity in the pupil edge location between at least a pair of images from the plurality of images.

8. An eye tracking system comprising:
    a detection module configured to detect a glint pattern, representative of an illumination pattern generated by a plurality of light sources, and a pupil edge of an eye in a plurality of images;
    an analysis module coupled to the detection module and configured to estimate a distance from an array camera, that generated the plurality of images, to the pupil edge based on a three-dimensional position of a corneal center of curvature of the eye; and
    a processing unit coupled to the analysis module and the detection module and configured to generate a pupil image based on selected ones of the plurality of images, the glint pattern, and an estimated distance to the eye, and determine a gaze vector based on the pupil image and the glint pattern.

9. The eye tracking system of claim 8, further comprising a light source selector module, coupled to the processing module, configured to activate and/or deactivate one or more of the plurality of light sources in response to a glint of the glint pattern interfering with the pupil edge in at least one of the plurality of images.

10. The eye tracking system of claim 8, further comprising a tracking module coupled to the processing module and configured to track a gate vector.

11. The eye tracking system of claim 9, wherein the analysis module is further configured to determine a region-of-interest within a field of view of an army camera and adjust the illumination pattern by activating or deactivating particular ones of the plurality of light sources to keep the illumination pattern within the region of interest.

12. The eye tracking system of claim 10, wherein the processing unit is further to generate the pupil image from the plurality of images such that the pupil image has a higher resolution than any one of the plurality of images.

13. The eye tracking system of claim 8, wherein the processing unit is further to generate the pupil image from the selected ones of the plurality of images such that only those images not having a glint interfering with the pupil edge are used in the pupil image.

14. A non-transitory machine-readable medium comprising instructions for eye tracking, which when executed by a machine, cause the machine to:
   obtain a plurality of images of the eye from an array camera;
   detect glint positions and a pupil edge of the eye in the plurality of the images;
   estimate a distance from the array camera to the pupil edge based on the glint positions;
   generate a pupil image based on the plurality of images, the glint positions, and an estimated distance to the eye based on the estimated distance from the array camera to the pupil edge; and
   determine a pupil center position based on the pupil image and the glint positions.

15. The machine readable medium of claim 14, wherein the machine is further caused to estimate the distance of the pupil edge from the array camera based on the detected glint positions in each image, a location of the array camera relative to light sources, corneal curvature of the eye, and a three-dimensional position of a corneal center of curvature.

16. The machine readable medium of claim 14, wherein the machine is further caused to obtain the plurality of images of the eye from each camera of the array camera.

17. The machine readable medium of claim 14, wherein the machine is further caused to generate the pupil image by selecting one of the plurality of images in which the pupil edge is not obscured by a glint.

18. The machine readable medium of claim 14, wherein the machine is further caused to determine a gaze vector based on the pupil center position, the glint positions, and one of an eyeball model using Purkinje images, a global head model, or an active appearance model.

19. The machine readable medium of claim 14, wherein the machine is further caused to activate or deactivate a plurality of light sources based on detected interference of one or more glints, resulting from respective ones of the plurality of light sources, with the pupil edge.

* * * * *